United States Patent [19]
Ennis, III et al.

[11] Patent Number: 5,290,258
[45] Date of Patent: Mar. 1, 1994

[54] SYRINGE FOR ADMINISTERING SEQUENTIALLY MULTIPLE DOSES OF A MEDICAMENT

[75] Inventors: James F. Ennis, III, Preston, Conn.; Mark Anderson, Hudson, Wis.

[73] Assignee: Genesis Industries, Inc., Elmwood, Wis.

[21] Appl. No.: 918,705

[22] Filed: Jul. 27, 1992

[51] Int. Cl.$^5$ .............................. A61M 5/178
[52] U.S. Cl. ........................ 604/215; 401/281; 222/548; 604/173
[58] Field of Search ............... 222/330, 548; 604/212, 604/258, 215, 173, 192, 187, 208–211; 401/281

[56] References Cited

U.S. PATENT DOCUMENTS

| | | | |
|---|---|---|---|
| 2,772,032 | 11/1956 | Patillo | 222/230 |
| 2,782,784 | 2/1957 | Ritter | 604/212 |
| 3,100,589 | 8/1963 | Love, Jr. | 222/548 |
| 3,129,860 | 4/1964 | Foster | 222/548 |
| 3,325,066 | 6/1967 | Allen | 222/548 |
| 3,595,231 | 7/1971 | Pistor | 604/173 |
| 4,552,155 | 11/1985 | Etherington et al. | 222/548 |
| 4,695,273 | 9/1987 | Brown | 604/173 |
| 5,109,955 | 5/1992 | Clark | 222/330 |
| 5,188,293 | 2/1993 | Burton | 239/548 |

*Primary Examiner*—C. Fred Rosenbaum
*Assistant Examiner*—Chalin Smith
*Attorney, Agent, or Firm*—Edward H. Loveman

[57] ABSTRACT

This syringe for dispensing multiple doses of a liquid medicament one at a time has a cylindrical barrel for containing the medicament. At one end of the barrel is a single outlet opening. A plunger in the barrel discharges the medicament. A syringe cap rotatable mounted on the barrel has guide means restraining the cap against axial movement. Ratchet means on the cap and barrel permit only unidirectional rotation of the cap and sequentially retain the cap in equally spaced detent positions on the barrel. Nozzles on top of the cap have passages for ejecting the medicament. Each passage terminates in a hole in the top of the cap. Only one nozzle at a time communicates with the barrel vis the outlet opening in each detent position of the cap on the barrel.

10 Claims, 2 Drawing Sheets

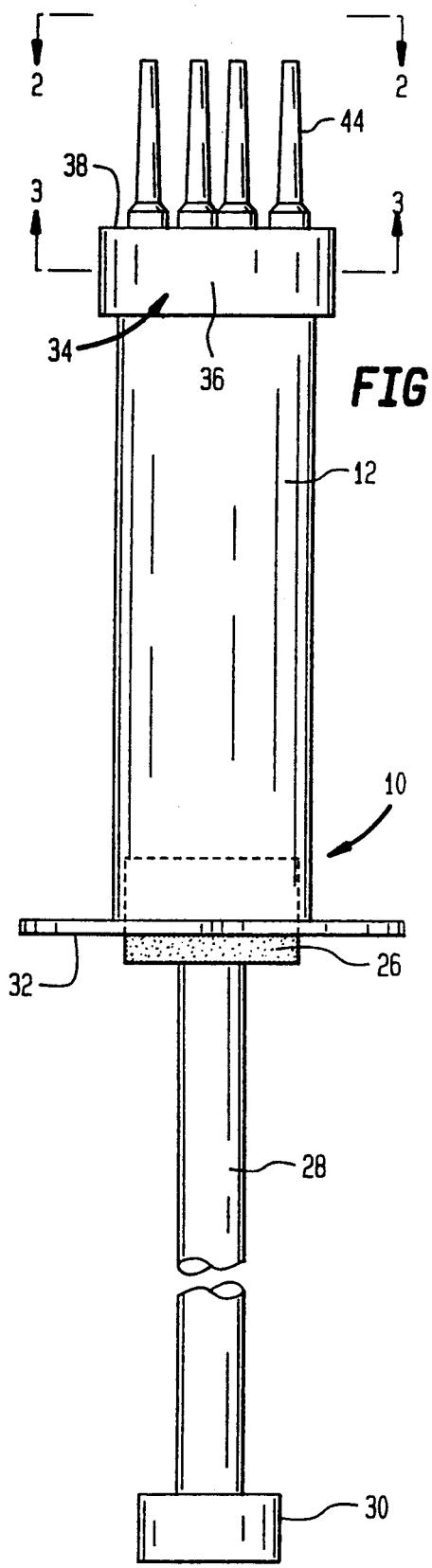
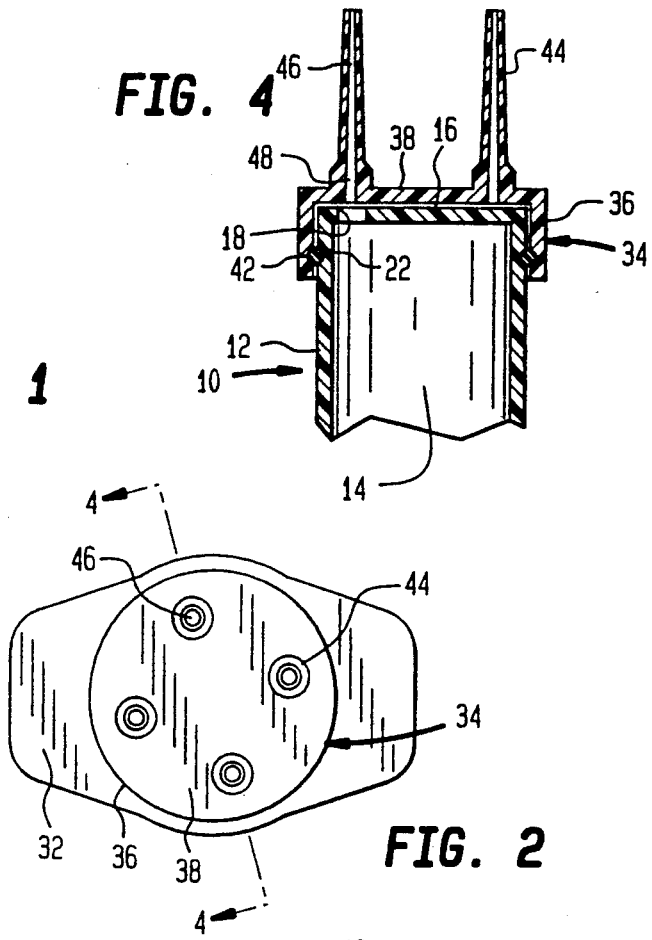
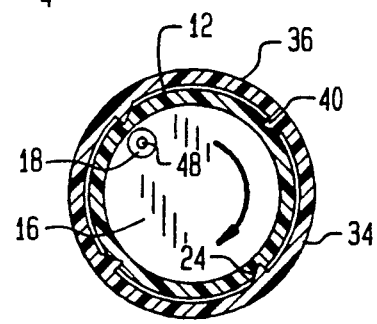
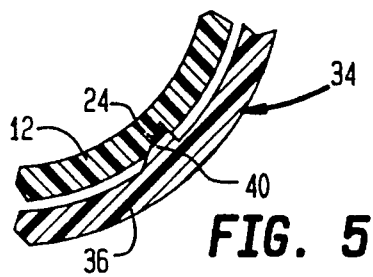

SYRINGE FOR ADMINISTERING SEQUENTIALLY MULTIPLE DOSES OF A MEDICAMENT

BACKGROUND OF THE INVENTION

1. Field of the Invention

This invention concerns the art of syringes; and more specifically this invention concerns syringes used for multiple injections of a medicinal fluid from a single syringe; and more particularly, this invention concerns a syringe having multiple nozzles arranged to permit only one nozzle at a time to inject medicinal fluid.

2. Description of the Prior Art

Heretofore it has been conventional to employ a syringe with a single nozzle to inject medicinal fluid into an animal's teats. This has proven very objectionable, since the use of the same syringe nozzle for all four teats of an animal, such as a cow, where one or more teats may be infected, exposes the animal to infection of all teats as the syringe is used upon each of the teats in succession. When for reasons of economy or lack of time, a single syringe with a single nozzle is used to treat more than one animal, many animals in a herd can be infected by the single nonsterile infected syringe. This is extremely undesirable practice. The lack or loss of sterility of the syringe when it has been used only once constitutes a positive health hazard which must be avoided.

SUMMARY OF THE INVENTION

The present invention avoids the difficulties and disadvantages of prior syringes having a single nozzle, by providing a syringe having a unidirectional rotatable cap with four tapered nozzles. The cap has four ratchet or detent teeth arranged to define four rotational positions on the barrel of the syringe. In each one of the rotational detent or ratchet positions, there is communication established between a single outlet of the syringe barrel and one nozzle located at the medicament discharge position. The other nozzles are blocked off from the medicament in the syringe barrel. Each nozzle is used only once to inject the medicament into one teat of an animal's udder. Then the cap is turned and the next nozzle is cleared to discharge medicament into another teat of the udder. This procedure can be continued until all four nozzles have injected medicament into the four teats of the animal under treatment. Then the syringe is discarded. By this arrangement it is assured that medicament is administered to an animal under absolutely sterile conditions, and is used for only one animal.

These and other objects and many of the attendant advantages of this invention will be readily appreciated as the same becomes better understood by reference to the following detailed description when considered in connection with the accompanying drawings in which

BRIEF DESCRIPTION OF THE DRAWINGS

FIG. 1 is a side elevational view of a syringe embodying the invention, part of a piston rod being broken away;

FIG. 2 is a top end view taken along line 2—2 of FIG. 1;

FIG. 3 is an enlarged cross sectional view taken along line 3—3 of FIG. 1;

FIG. 4 is an enlarged fragmentary axial sectional view taken along line 4—4 of FIG. 2;

FIG. 5 is an enlarged fragmentary sectional view similar to a portion of FIG. 3, showing details of the unidirectional ratchet or detent structure of the syringe cap;

DESCRIPTION OF THE PREFERRED EMBODIMENTS

Figures 6, 7:
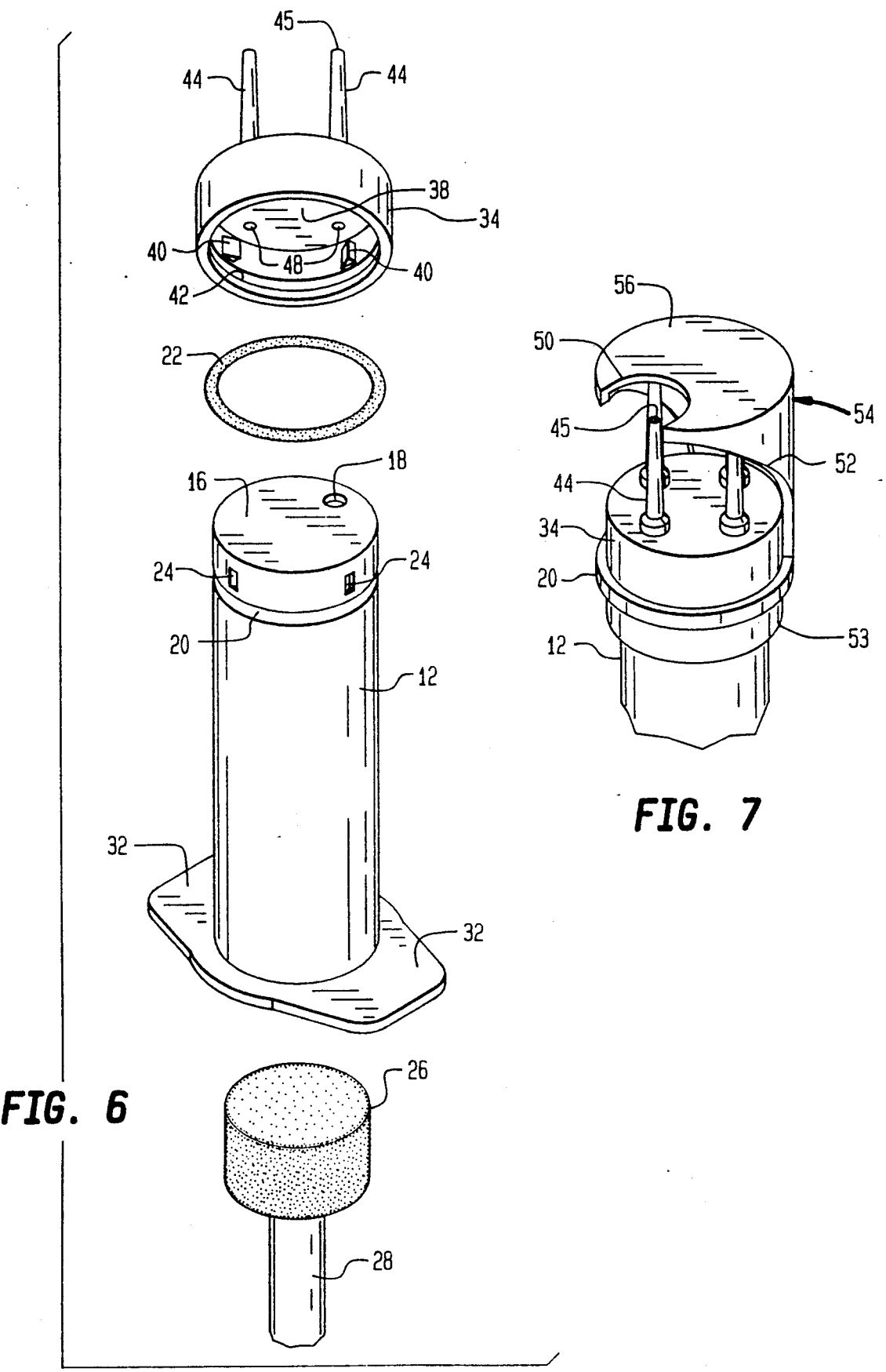
FIG. 6 is an exploded perspective view of an enlarged scale of parts of the syringe assembly shown in FIGS. 1-5.
FIG. 7 is a perspective view of a cover for the syringe assembly.

Referring now to the drawings wherein like reference characters designate like or corresponding parts throughout, there is illustrated in FIGS. 1-6, a syringe assembly generally designated by reference numeral 10, having a flexible cylindrical barrel 12 which can contain a desired quantity of liquid medicament 14. The barrel 12 has a closed circular top wall 16 provided with a single outlet hole 18 near the periphery of the wall 16. In the cylindrical wall of the barrel 12 is a circumferential groove 20 which receives and engages a snap ring or spring ring 22. Between the groove 20 and the top wall 16 are four circumferentially spaced wedge shaped recesses 24 forming part of the one-way ratchet or detent arrangement of the syringe 10. At the other end of the barrel 12 is a piston head or plunger 26 driven axially in the barrel 12 by a piston shaft 28 having a knob 30 at its outer end. A flange 32 which serves as a finger or hand gripping means is integral with the barrel 12 and extends radially outward.

The syringe 10 has a rotatable cap 34 formed with a cylindrical skirt 36 and a circular top wall 38. In the skirt 36 are four circumferentially spaced wedge shaped projections 40 each of which is engaged in a respective one of the recesses 24. When the cap 34 is rotated on the barrel 12, the projections 40 engage in the next adjacent recess 24 in the direction of rotation. Engagement takes place at 90° spaced positions in a detent, ratchet or snap action so that the cap 34 assumes four discrete definite positions on the barrel 12. A circumferential groove 42 is formed in the skirt 36 to receive and engage the outer side of the spring ring 22 so that the cap 34 is locked against axial movement of the barrel 12, and is limited to rotational motion in one direction only on the barrel 12 due to the slanted construction of the wedges 40 and wedge shaped recesses 24. On the top of wall 38 are four circumferentially spaced tapered integral nozzles 44. Each nozzle 44 has a discharge orifice or hole 45 and an axial passage 46 terminating in a hole 48 in the wall 38. When the cap 34 is rotated, one hole 48 at a time aligns axially with the outlet hole 18 in the top wall 16 of the barrel; see FIG. 3. Thus, the medicament 14 can be discharged through only one outlet hole 48 at a time. If the cap 34 is rotated out of engagement with the recesses 24, then all nozzle passages 46 are closed off from the interior of chamber 12.

It will be apparent that the projections 40 and the recesses 24 constitute a ratchet or detent arrangement in which only one nozzle 44 at a time can serve as an outlet for the medicament 14, in each detent position of the cap 34. The cap 34 is manually rotated in one direction only to set the cap 34 sequentially in each of the four detent positions spaced 90° apart.

If desired the syringe 10 may be fitted with a cover 54 rigidly mounted via a base 53 to the barrel 12, such as illustrated in FIG. 7. The cover 54 has a top face 56 with a hole 50 aligned with the outlet hole 18 in the top wall 16 (not illustrated) for permitting one of the nozzle holes 45 of the nozzle 44 to be aligned with the hole 50 and thereby permit dispensing medicament therefrom, while the other nozzles are covered by the top face 56 of the cover 54. The cover 54 may include a cutout 52 which permits the fingers of a user of the syringe 10 to grasp the cap 34 and rotate same to the next sequential detent position.

The cap 34, the cover 54 and the barrel 12 are preferable made of lightweight, inexpensive plastic such as polyethylene, polystyrene, or the like. After the medicament 14 is ejected from each nozzle 44, the entire syringe 10 can be discarded. When the syringe 10 is used for treating cows or other animals for mastitis or other infections, a desired quantity of medicament 14 will be injected into each teat in the animal's udder. A separate nozzle 44 will be used for each teat. When all four teats have been treated, the syringe 10 will be discarded. It will not be used again upon the same or other animal. In this way sterility of treatment is assured.

The syringe is characterized by its simplicity of construction, and ease of operation. Its use is safe and cannot infect healthy teats of other animals.

It should be understood that the foregoing relates to only a limited number of preferred embodiments of the invention which have been by way of example only, and that it is intended to cover all changes and modifications of the examples of the invention herein chosen for the purposes of the disclosure which do not constitute departures form the spirit and scope of the invention.

What is claimed:

1. A syringe for dispensing multiple doses of a liquid medicament one at a time sequentially comprising:

a cylindrical barrel for containing said medicament, said barrel having a closed circular wall at one end thereof, with a single outlet opening for said medicament in said end wall;

ejection means in said barrel for ejecting said medicament therefrom;

a syringe cap rotatably mounted on said end of said barrel;

guide means restraining said cap against axial movement on said barrel while permitting rotation of said cap, said cap having a circular top;

ratchet means on said cap and barrel permitting only unidirectional rotation of said cap on said barrel and sequentially retaining said cap in a plurality of detent positions on said barrel; and a plurality of nozzles on said top of said cap, each of said nozzles having a discharge orifice and an axial passage for ejection of said medicament from each of said nozzles, each of said passages terminating in a nozzle hole in said circular top so that one of said nozzle holes is aligned with said opening in said end wall of said barrel in each of said detent positions of said cap on said barrel, whereby said medicament can be discharged from each nozzle in turn only when said cap is located in a corresponding detent position of said cap.

2. A syringe as claimed in claim 1, wherein said cap and said barrel have spaced opposing circular grooves receiving said guide means to constrain said cap to rotational movement of said barrel while preventing relative axial movement between said cap and said barrel.

3. A syringe as claimed in claim 1, wherein said cap has a cylindrical skirt surrounding said one end of said barrel, said skirt and barrel having opposing circumferential grooves, said guide means comprising a spring ring engaging in said grooves in said skirt and said barrel.

4. A syringe as claimed in claim 3, wherein said ratchet means comprises circumferentially spaced mating angular projections on said skirt and said barrel, to limit said cap to unidirectional rotation on said barrel and to hold said cap sequentially in each of said detent positions on said barrel.

5. A syringe as claimed in claim 4, wherein said ejection means comprises a plunger movable axially in said barrel.

6. A syringe as claimed in claim 4, wherein said nozzles are tapered and smooth to facilitate entry thereof into an animal being treated.

7. A syringe as claimed in claim 4, wherein said nozzles, said nozzle holes and said detent positions are four in number.

8. A syringe as claimed in claim 7, wherein said nozzles, said nozzle holes, and said detent positions of said cap are angularly spaced apart by 90° around said cap, so that said cap is rotated through four equal angles to move through said detent positions of said cap.

9. A syringe as claimed in claim 1, wherein said cap and said barrel are made of flexible, lightweight, inexpensive, expendable material, so that said cap and barrel can be discarded as a unit after said medicament is discharged from all of said nozzles.

10. A syringe as claimed in claim 1, further including a cover fixedly mounted on said barrel and having a top surface covering all but one of said discharge orifices of said nozzles said top surface having a hole theretnrough aligned with said opening in said end wall whereby only said nozzle of said one discharge orifice is aligned with said opening in said end wall.

* * * * *